United States Patent
Choi et al.

(10) Patent No.: US 7,375,030 B2
(45) Date of Patent: May 20, 2008

(54) METHOD TO ASSAY SACRIFICIAL LIGHT ABSORBING MATERIALS AND SPIN ON GLASS MATERIALS FOR CHEMICAL ORIGIN OF DEFECTIVITY

(75) Inventors: Hok-Kin Choi, San Jose, CA (US); Robert P. Meagley, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 11/440,933

(22) Filed: May 25, 2006

(65) Prior Publication Data

US 2006/0234495 A1    Oct. 19, 2006

Related U.S. Application Data

(62) Division of application No. 10/750,199, filed on Dec. 30, 2003, now Pat. No. 7,089,785.

(51) Int. Cl.
    *H01L 21/4763*    (2006.01)

(52) U.S. Cl. .............................. 438/637; 257/E21.579
(58) Field of Classification Search ............... 438/637; 73/61.52; 257/E21.579
    See application file for complete search history.

(56) References Cited

U.S. PATENT DOCUMENTS

| | | | |
|---|---|---|---|
| 6,329,118 B1 | 12/2001 | Hussein et al. |
| 6,365,529 B1 | 4/2002 | Hussein et al. |
| 6,448,185 B1 | 9/2002 | Andideh et al. |
| 6,506,692 B2 | 1/2003 | Andideh et al. |

*Primary Examiner*—Fernando L. Toledo
(74) *Attorney, Agent, or Firm*—Blakely, Sokoloff, Taylor & Zafman LLP

(57) ABSTRACT

Numerous embodiments of a method to assay sacrificial material are disclosed. In one embodiment, a sacrificial material may be analyzed by high performance liquid chromatography. Chemical markers that correlate with material contaminants in the sacrificial material may be identified.

15 Claims, 9 Drawing Sheets

METHOD TO ASSAY SACRIFICIAL LIGHT ABSORBING MATERIALS AND SPIN ON GLASS MATERIALS FOR CHEMICAL ORIGIN OF DEFECTIVITY

RELATED APPLICATION

This is a divisional application of U.S. patent application Ser. No. 10/750,199, filed on Dec. 30, 2003 now U.S. Pat. No. 7,089,785.

TECHNICAL FIELD

Embodiments of the present invention relate to the field of semiconductor processing and the fabrication of integrated circuits.

BACKGROUND

Dual damascene metal interconnects may enable reliable low cost production of integrated circuits using sub 0.18 micron process technology. To enable such interconnects to realize their full potential, one method for making a semiconductor device involves a first etched region (e.g., a via or trench) that is filled with a sacrificial light absorbing material (SLAM), after that region has been formed within a dielectric layer. The SLAM may comprise a dyed spin-on-glass (SOG) that has dry etch properties similar to those of the dielectric layer and light absorbing properties that enable the substrate to absorb light during lithography. After the first etched region is filled with the SLAM, a second etched region (e.g., a trench if the via is already formed or a via if the trench is already formed) is formed within the dielectric layer. Most of the SLAM may be removed as that second etched region is formed. Remaining portions of the SLAM are removed by a subsequent wet etch procedure.

The SLAM process reduces, or eliminates, substrate reflection and the need for high etch selectivity. However, material defects in the SLAM and SOG materials may adversely affect dual damascene via and trench formation. Current methods known in the art for the functional characterization of SLAM and SOG materials involve indirect methods that provide characterization based on optical or surface analysis. However, these methods are inadequate because they fail to provide information about what the specific defects in the material may be.

BRIEF DESCRIPTION OF THE DRAWINGS

Embodiments of the present invention are illustrated by way of example, and not limitation, in the figures of the accompanying drawings in which.

DETAILED DESCRIPTION

In the following description, numerous specific details are set forth such as examples of specific materials or components in order to provide a thorough understanding of embodiments of the present invention. It will be apparent, however, to one skilled in the art that these specific details need not be employed to practice embodiments of the present invention. In other instances, well known components or methods have not been described in detail in order to avoid unnecessarily obscuring embodiments of the present invention.

The terms "on," "above," "below," "between," and "adjacent" as used herein refer to a relative position of one layer or element with respect to other layers or elements. As such, a first element disposed on, above or below another element may be directly in contact with the first element or may have one or more intervening elements. Moreover, one element disposed next to or adjacent another element may be directly in contact with the first element or may have one or more intervening elements.

Any reference in the specification to "one embodiment" or "an embodiment" means that a particular feature, structure, or characteristic described in connection with the embodiment is included in at least one embodiment of the claimed subject matter. The appearances of the phrase, "in one embodiment" in various places in the specification are not necessarily all referring to the same embodiment.

Numerous embodiments of a method for direct chemical analysis of sacrificial or dyed coating material are described. In one embodiment of the present invention, a sacrificial light absorbing material (SLAM) may be analyzed by high performance liquid chromatography (HPLC) prior to the SLAM being deposited on a substrate (e.g., active and passive devices that are formed on a silicon wafer). In another embodiment of the present invention, a spin-on-glass (SOG) material or a combination of SLAM and SOG may be analyzed by HPLC prior to or during a process to form semiconductor device. An in-process analysis of SLAM and SOG allows for the detection of integrated performance deficiencies (i.e., defects) by identifying chemical markers strongly correlating with SLAM or SOG defects. In one embodiment, the HPLC analysis of SLAM and SOG materials may be done in conjunction with a dual damascene process.

Figure 1A:
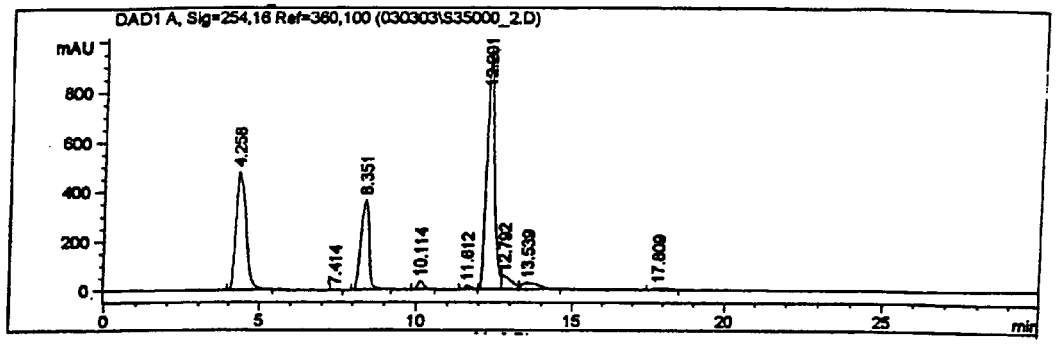
FIG. 1A illustrates an HPLC chromatogram of a sacrificial light absorbing material.
Figure 1B:
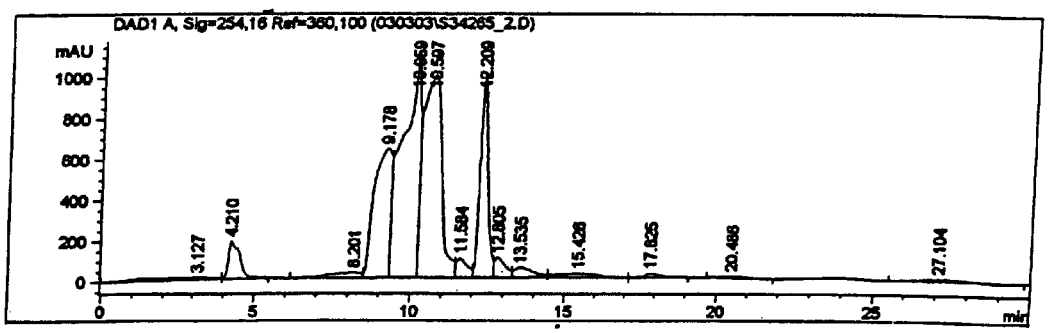
FIG. 1B illustrates another HPLC chromatogram of a sacrificial light absorbing material.
Figure 1C:
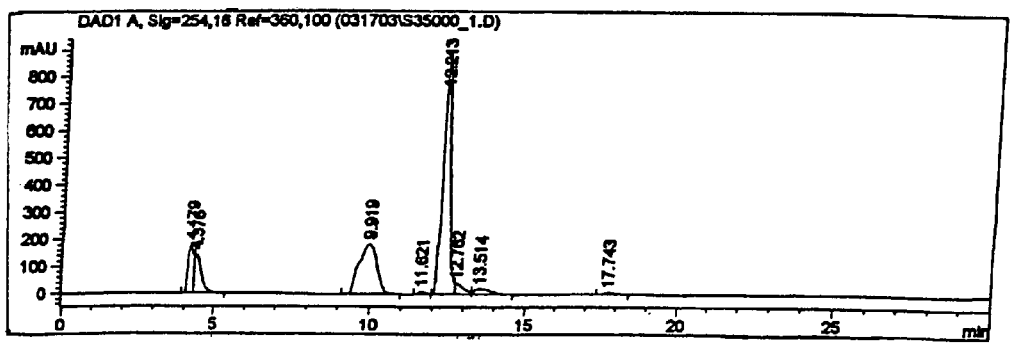
FIG. 1C illustrates another HPLC chromatogram of a sacrificial light absorbing material.

FIGS. 1A-1C illustrate examples of chromatograms for SLAM samples assayed by HPLC. In one method, the assays may be performed using a liquid chromatography system (e.g., an Agilent 1100 HPLC system, made by Agilent Technologies, Inc., of Palo Alto, Calif.). A methanol/deionized water mixture may be used as an eluent with a flow rate from about 0.3 to about 1.0 milliliters/minute (ml/mn). The size of the SLAM sample may be about 5 microliters to about 20 microliters. This mixture may be forced under high pressure through an analytical column (e.g., a Nucleosil® C18 chromatographic analytical column). The analytical column may be about 5 centimeters to about 25 centimeters in length. The column may be packed with silicon dioxide ($SiO_2$) cultured with hydrophobic carbon-chains.

In general, chromatographic separation is based on the difference in the surface interactions of the analyte and eluent molecules. During a run, a chromatographic band may spread due to uneven flows around and inside porous particles, slow adsorption kinetics, longitudinal diffusion, and other factors to produce band broadening of the chromatographic zone. In general, the longer the component is retained on a column, the more broad its zone (i.e., peak on the chromatogram). Separation performance depends on both component retention and band broadening. Band broadening is, in general, a kinetic parameter, dependent on the absorbent particle size porosity, pore size, column size, shape, and packing performance. Retention reflects molecular surface interactions and depends on the total adsorbent surface. Following the chemical separation of the SLAM sample, the resulting signals may be identified/detected with an ultraviolet/visual and mass spectroscopy system (UV/VIS-MS). In one embodiment, the monitoring wavelength of the UV/VIS detector for SLAM may be between about 240 nanometers to about 260 nanometers.

FIG. 1A illustrates an HPLC chromatogram of a SLAM assay having little or no material defects. The SLAM signal near a retention time between about 8 and 9 minutes is clean and uncontaminated. The other signals are related to either solvents and/or starting materials which are used to synthesize SLAM. FIG. 1B illustrates an HPLC chromatogram of a SLAM assay indicating SLAM contamination. The SLAM signal near a retention time between about 8 and 9 minutes show significant contamination as contaminants and other side product signals overlap with the SLAM signal. FIG. 1C illustrates an HPLC chromatogram for a SLAM sample left near room temperature (e.g., 21-23° C.) for 10 days. Compared to the chromatogram illustrated in FIG. 1A, the SLAM signal near about 8 and 9 minutes has broadened.

With respect to the chromatograms of FIGS. 1A-1C, assaying SLAM with HPLC provides advantages of characterizing SLAM not found in other methods known in the art. For example, with respect to FIGS. 1A and 1B, a SLAM sample may be tested to determine the existence of contaminants which may be followed by a monitoring procedure (e.g., UV/VIS-MS) to specifically identify each contaminant. With respect to FIGS. 1A and 1C, the broadening of the SLAM signal may indicate material degradation over time. In one embodiment, the chromatograph of FIG. 1C is provided to show that SLAM material may degrade over a certain period of time. It may be appreciated that HPLC assays may be done not only at 10 days, but at any other time to determine material degradation (e.g., 14, 30, 90 days). As such, characterizing SLAM with an HPLC assay enables direct chemical analysis of the material to identify process relevant changes that may be directly related to material performance issues (e.g., when SLAM is used during a semiconductor process such as dual damascene). In an alternative embodiment of the present invention, HPLC assay may be used to analyze other types of dye coating material, such as SOG.

HPLC assay may also be used to improve the performance of SLAM and SOG materials. For example, a first assay of a SLAM sample may result in a chromatogram showing the existence of one or more contaminants, similar to that shown in FIG. 1B. One or more cleaning or purification techniques may be done on the material followed by a second assay of the SLAM material to verify that the contaminants no longer exist (i.e., the chromatogram has a similar result to that shown in FIG. 1A). This method may be repeated as necessary until all the contaminants have been identified and removed from the SLAM or SOG materials. As such, performance of SLAM and SOG materials may be linked to the optimization of the composition profile obtained by HPLC assay and other assay methods described herein.

Another advantage of HPLC assay for dye coating materials such as SLAM and SOG is the detection of material defects in process (i.e., during semiconductor fabrication).

As such, prolonged test periods or delays caused by waiting for results of tests performed outside of a fabrication setting are avoided. In a method of the present invention, first conductive layer 101 is formed on substrate 100. Substrate 100 may be any surface, generated when making an integrated circuit, upon which a conductive layer may be formed. Substrate 100 thus may include, for example, active and passive devices that are formed on a silicon wafer such as transistors, capacitors, resistors, diffused junctions, gate electrodes, local interconnects, etc. Substrate 100 also may include insulating materials (e.g., silicon dioxide, either undoped or doped with phosphorus (PSG) or boron and phosphorus (BPSG); silicon nitride; silicon oxynitride; or a polymer) that separate such active and passive devices from the conductive layer or layers that are formed on top of them, and may include previously formed conductive layers.

Conductive layer 101 may be made from materials conventionally used to form conductive layers for integrated circuits. For example, conductive layer 101 may be made from copper, a copper alloy, aluminum or an aluminum alloy, such as an aluminum/copper alloy. Alternatively, conductive layer 101 may be made from doped polysilicon or a silicide, e.g., a silicide comprising tungsten, titanium, nickel or cobalt.

Conductive layer 101 may include a number of separate layers. For example, conductive layer 101 may comprise a primary conductor made from an aluminum/copper alloy that is sandwiched between a relatively thin titanium layer located below it and a titanium, titanium nitride double layer located above it. Alternatively, conductive layer 101 may comprise a copper layer formed on underlying barrier and seed layers.

Conductive layer 101 may be formed by a chemical vapor or physical deposition process, like those that are well known to those skilled in the art. Alternatively, where copper is used to make conductive layer 101, a conventional copper electroplating process may be used. Other techniques for applying an electroplating process to form copper containing conductive layers are well known to those skilled in the art. Although a few examples of the types of materials that may form conductive layer 101 have been identified here, conductive layer 101 may be formed from various other materials that can serve to conduct electricity within an integrated circuit.

After forming conductive layer 101 on substrate 100, barrier layer 102 is formed on conductive layer 101. Barrier layer 102 will serve to prevent an unacceptable amount of copper, or other metal, from diffusing into dielectric layer 103. Barrier layer 102 also acts as an etch stop to prevent subsequent via and trench etch procedures from exposing conductive layer 101 to subsequent cleaning procedures. Barrier layer 102 preferably is made from silicon nitride, but may be made from other materials that can serve such functions, e.g., titanium nitride or oxynitride, as is well known to those skilled in the art.

When formed from silicon nitride, a chemical vapor deposition process may be used to form barrier layer 102. Barrier layer 102 should be thick enough to perform its diffusion inhibition and etch stop functions, but not so thick that it adversely impacts the overall dielectric characteristics resulting from the combination of barrier layer 102 and dielectric layer 103. To balance these two factors, the thickness of barrier layer 102 preferably should be less than about 10% of the thickness of dielectric layer 103.

Figure 2A:
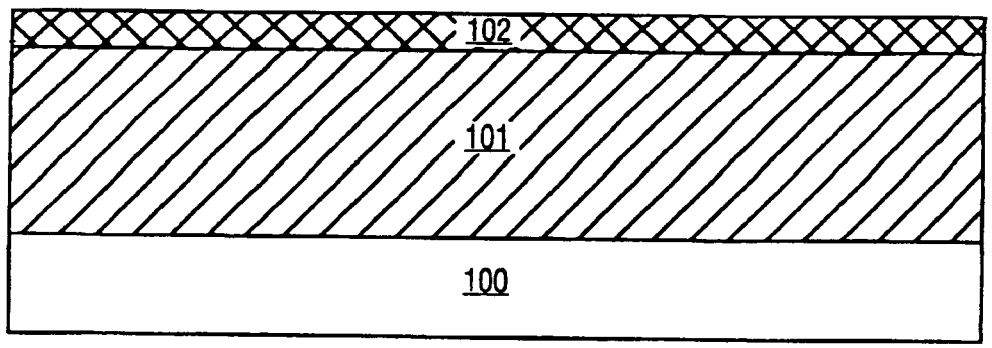
FIGS. 2A-2H illustrate cross-sections that reflect structures that may result after certain procedures are used to make a dual damascene device in one embodiment of a method of the present invention.

Conductive layer 101 and barrier layer 102 may be planarized, after they are deposited, using a CMP procedure. FIG. 2A illustrates a cross-section of the structure that results after conductive layer 101 and barrier layer 102 have been formed on substrate 100.

Dielectric layer 103 is then formed on top of barrier layer 102. Dielectric layer 103 preferably comprises silicon dioxide, which is deposited on the surface of barrier layer 102 using a conventional plasma enhanced chemical vapor deposition (PECVD) process that employs tetraethylorthosilicate (TEOS) as the silicon source. Although preferably made of silicon dioxide, dielectric layer 103 may be made from other materials that may insulate one conductive layer from another, as will be apparent to those skilled in the art. For example, dielectric layer 103 may comprise an organic polymer selected from the group that includes polyimides, parylenes, polyarylethers, polynaphthalenes, and polyquinolines, or copolymers thereof. Alternatively, dielectric layer 103 may comprise fluorinated silicon dioxide or a porous silicon dioxide, e.g., silicon dioxide doped with carbon. Dielectric layer 103 preferably has a thickness of between about 2,000 and about 20,000 angstroms.

Figure 2B:
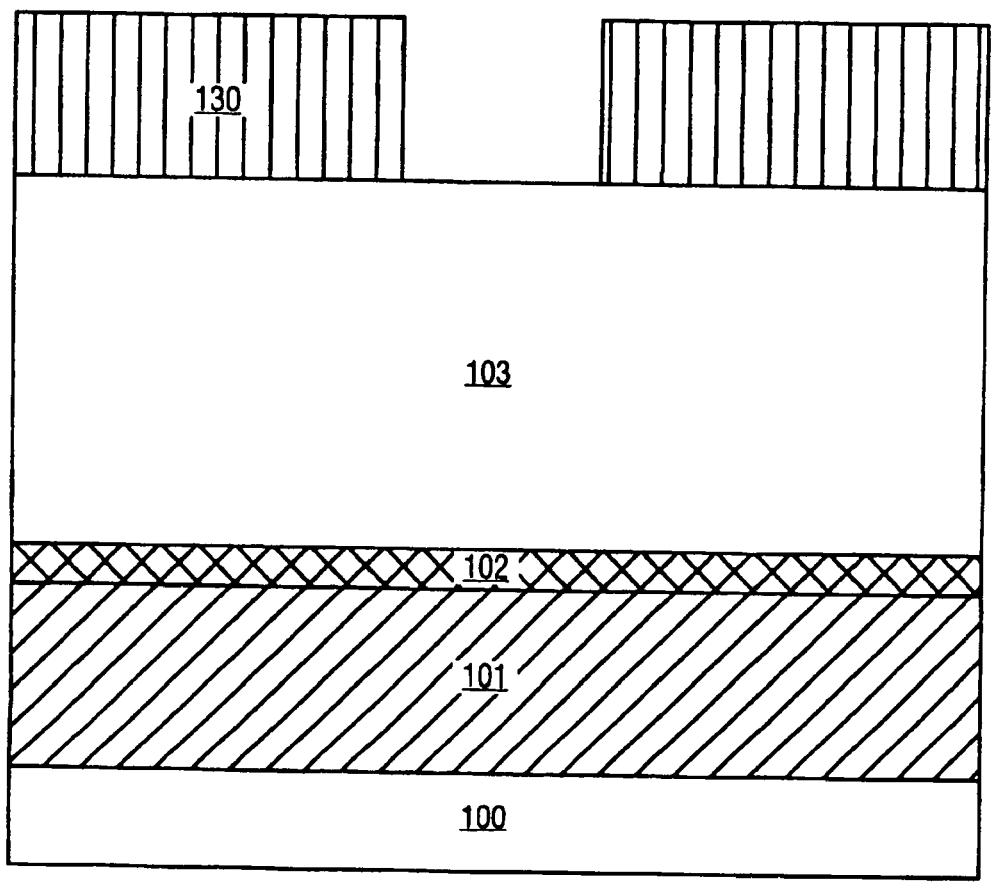

After forming dielectric layer 103, a photoresist layer 130 is patterned on top of it to define a via formation region for receiving a subsequently formed conductive layer that will contact conductive layer 101. Photoresist layer 130 may be patterned using conventional photolithographic techniques, such as masking the layer of photoresist, exposing the masked layer to light, then developing the unexposed portions. The resulting structure is shown in FIG. 2B. Although this particular embodiment does not specify forming a hard mask on top of dielectric layer 103 prior to applying the photoresist, such a hard mask may be desirable when using certain types of material to form dielectric layer 103, as is well known to those skilled in the art.

After photoresist 130 is patterned, via 107 is etched through dielectric layer 103 down to barrier layer 102. Conventional process methods for etching through a dielectric layer may be used to etch the via, e.g., a conventional anisotropic dry oxide etch process. When silicon dioxide is used to form dielectric layer 103, the via may be etched using a medium density magnetically enhanced reactive ion etching system ("MERIE system") using fluorocarbon chemistry. When a polymer is used to form dielectric layer 103, a forming gas chemistry, e.g., one including nitrogen and either hydrogen or oxygen, may be used to etch the polymer.

Figure 2C:
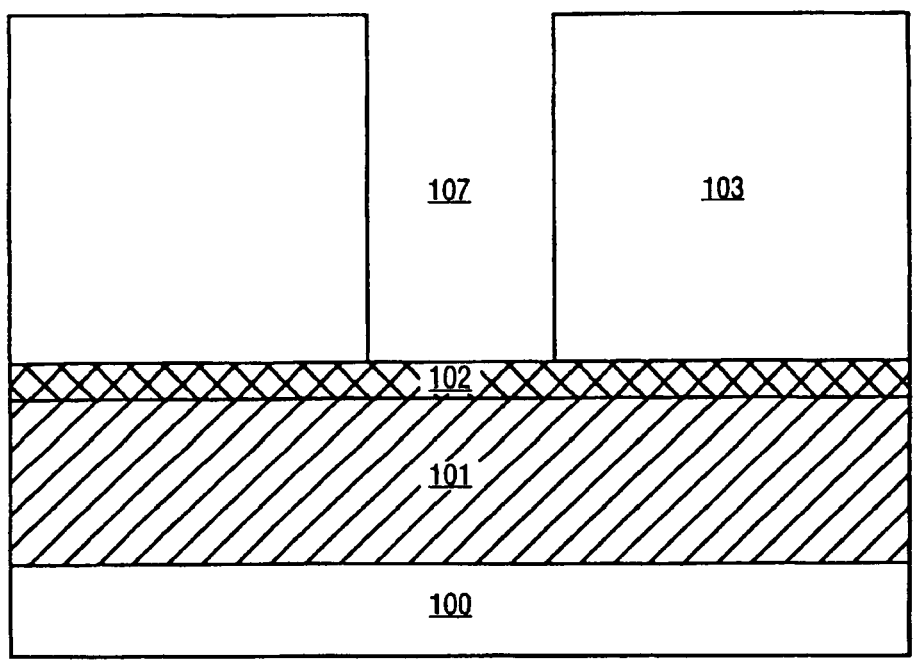

Barrier layer 102 acts as an etch stop to protect conductive layer 101 from being exposed to subsequent process procedures. Because of non-uniformity in the thickness of dielectric layer 103, and oxide etch variability, an over-etch procedure may be necessary. Such an over-etch procedure may consume about 20-30% of barrier layer 102. Conventional post etch ashing and via clean procedures may follow the via etch procedure to produce the structure shown in FIG. 2C. Via 107 may be cleaned by using a conventional HF in ethylene glycol based wet etch process, as is well understood by those skilled in the art.

In processes that form a hard masking layer on top of dielectric layer 103, a two-procedure process may be used to etch the via—the first procedure etching through the exposed portion of the hard mask and the second procedure etching through the underlying dielectric layer.

Figure 2D:
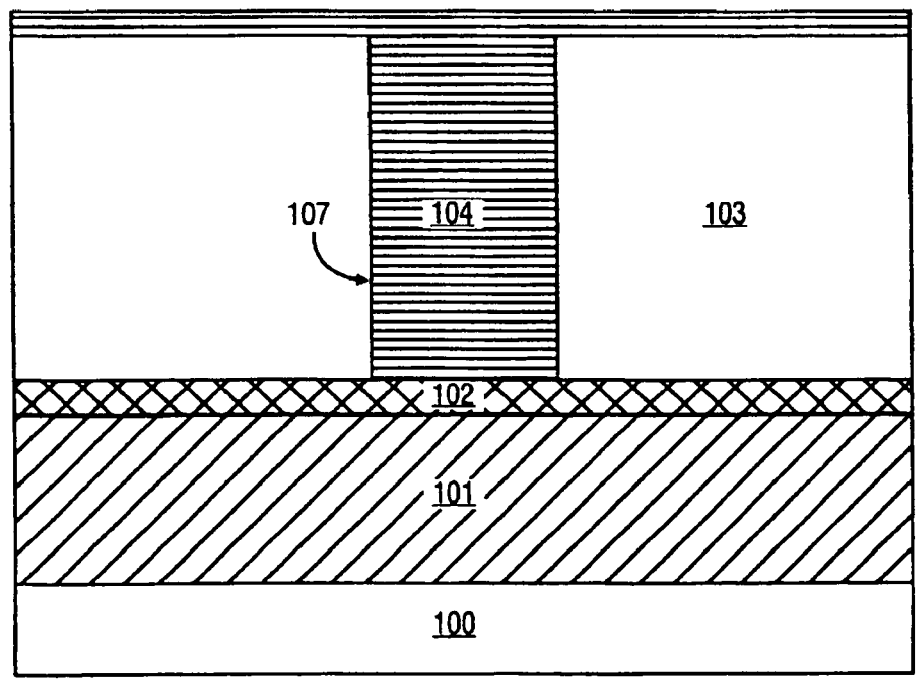

After via 107 is formed through dielectric layer 103, via 107 is filled with SLAM 104, generating the structure shown in FIG. 2D. SLAM 104 has dry etch properties similar to those of dielectric layer 103. Preferably, SLAM 104 comprises a spin-on-polymer (SOP) or spin-on-glass (SOG) that is deposited by spin coating between about 500 and about 3,000 angstroms of the material onto the surface of the device, using conventional process methods. Although only a thin layer remains on the surface of the device, such a spin coating process causes SLAM 104 to substantially, or completely, fill via 107. In this embodiment of the present invention, SLAM 104 preferably should etch at a slightly faster rate than dielectric layer 103, when subjected to the chosen dry etch chemistry.

Whether an SOP or SOG material is used for SLAM 104 may depend upon the type of material used to form dielectric layer 103. If dielectric layer 103 is formed from silicon dioxide, using an SOG material to form SLAM 104 should yield a better match between their respective etch rates. If dielectric layer 103 is formed from a polymer, then forming SLAM 104 from an SOP material may produce a combination of materials having the desired selectivity. If dielectric layer 103 includes a porous silicon dioxide, whether an SOG or SOP material is etched at a rate that more closely matches the etch rate of the dielectric layer may depend upon the amount of carbon that is included in the porous silicon dioxide layer.

In addition to having dry etch properties like those of dielectric layer 103, SLAM 104 should uniformly fill via 107 and have a wet etch rate that is significantly faster than the wet etch rate for dielectric layer 103. Such dry etch properties should enable removal of substantially all of the SLAM from the bottom of the via at the end of the trench etch process. The uniform fill characteristic minimizes void formation, which could jeopardize the integrity of the filling and/or may expose the underlying silicon nitride layer, for an undesirable extended period of time, to etch chemistry used to form the trench. The selectivity of SLAM 104 to the wet etch enables removal of that material from the surface of the device, as well as from inside via 107.

In one embodiment of the present invention, SLAM 104 may be analyzed by HPLC to determine or identify any material defects in the SLAM composition. For example, SLAM 104 may be assayed by HPLC prior to filling via 107 with SLAM 104. Material defects or contaminants may prevent SLAM 104 from having dry etch properties similar to those of dielectric layer 103. In one embodiment, SLAM 104 may be analyzed in a manner similar to that described above with respect to FIGS. 1A-1C. If a sample of SLAM 104 is determined to possess contaminants (e.g., FIG. 1B) or show degradation (e.g., FIG. 1C), via 107 may not be filled with SLAM 104. However, if a sample of SLAM 104 is shown to be free of contaminants or show no signs of degradation (e.g., FIG. 1A), via 107 may be filled with SLAM 104.

When SLAM 104 is transparent, high substrate reflectivity (and reflectivity variation across devices), which results during the exposure procedure of the lithographic process used to define the trench, may adversely affect the ability to control CDs and their uniformity. That effect may become more pronounced as those CDs shrink.

Using a dyed SOP or SOG for SLAM 104 should enable control of such substrate reflectivity. By dyeing such a base material with certain organic or inorganic substances, that base material may become opaque. By using a dyed base material for SLAM 104, changes in substrate reflectivity may be reduced, which may enable the photolithographic process to produce improved results. The organic or inorganic material chosen for the dye preferably should absorb light that is used during the exposure procedure of the photolithographic process. Preferably, the quantity and type of light absorbing dye, which is added to the base SLAM, should enable appreciable absorption of light having a wavelength identical to that used to expose the photoresist to pattern it. For example, the dye type and amount, and the type of base material, used to form the SLAM may be selected and tuned to absorb i-line (e.g., 365 nm), deep ultraviolet (e.g., 248 nm and 193 nm), or shorter, wavelengths.

When selecting the type of dye to add to the SOP, SOG, or other SLAM, and the amount to add, one should ensure that the resulting composition does not compromise the filling capability of the SLAM. In addition, when selecting the kind of dye used, and the amount used, one should ensure that the wet etch selectivity of the resulting dyed SLAM to the dielectric layer remains high, and that the dry etch selectivity of the SLAM to the dielectric layer is close to 1:1.

In an alternative embodiment of the present invention, dyed SOP and SOG materials used for SLAM 104 may also be analyzed by HPLC in a manner similar to that described above with respect to FIGS. 1A-1C. Material defects in the SOP and SOG materials may result in substrate reflectivity that is not reduced, preventing the photolithographic process from producing improved results.

Although this embodiment of the present invention describes using a dyed base material to reduce substrate reflectivity in the context of a process for making an integrated circuit that includes a dual damascene interconnect, this technique may be used in many other applications. As a general matter, coating a substrate with such a dyed material should suppress light reflection from underlying layers and, hence, improve lithographic performance. For that reason, embodiments of the present invention is not limited to application of this technique in the dual damascene context, but instead applies broadly to any process that benefits from the use of a non-reflective surface to improve lithography. Similarly, the dye based material may be analyzed by HPLC in process prior to their use in a process that benefits from a non-reflective surface.

Figure 2E:
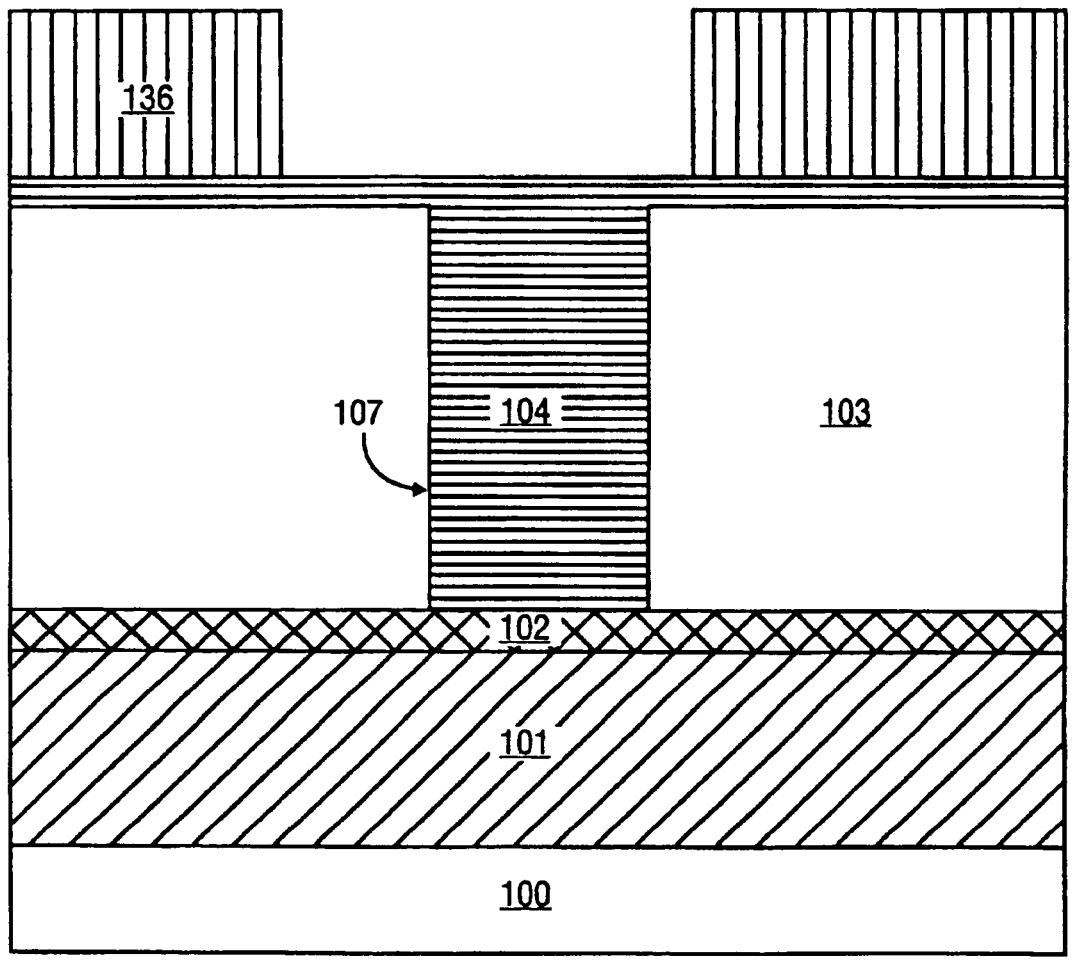
Figure 2F:
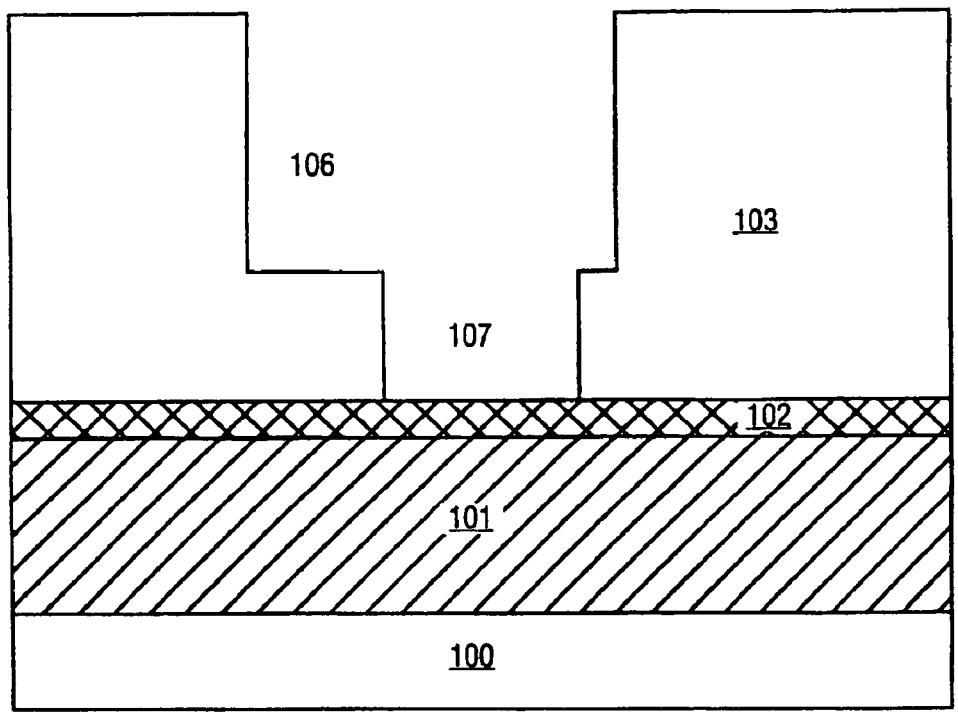

After filling via 107 with SLAM 104, photoresist layer 136 is applied on top of layer 104, then patterned to define a trench formation region. Photoresist layer 136 may be patterned using conventional photolithographic techniques. The resulting structure is shown in FIG. 2E. Following that photoresist patterning procedure, trench 106 is etched into dielectric layer 103 to form the structure shown in FIG. 2F.

The etching process is applied for a time sufficient to form a trench having the desired depth. The etch chemistry chosen to etch trench 106 preferably should remove SLAM 104 at a slightly faster rate than it removes dielectric layer 103, to avoid formation of defects. Trench 106 may be etched using the same equipment and etch chemistry that had been used previously to etch via 107. As with the via etch procedure, barrier layer 102 may act as an etch stop during the trench etching process, protecting the underlying conductive layer from the etch procedure and any subsequent ashing or cleaning procedures. In addition, the presence of any portion of SLAM 104 that remains at the bottom of via 107 after the trench etch procedure may help ensure that conductive layer 101 will not be affected by the trench etch process.

By filling via 107 with a SLAM having dry etch characteristics like those of dielectric layer 103, the trench lithography process effectively applies to a substantially "hole-free" surface, similar to one without vias. By selecting an appropriate SOP or SOG material for SLAM 104, and an appropriate etch chemistry, trench 106 may be etched into dielectric layer 103 at a rate that is almost as fast as SLAM 104 is removed. Such a process protects the underlying barrier layer 102 during the etching of trench 106. Such a process thus permits the use of a trench etch chemistry that produces superior trench and via profiles without having to consider the effect such etch chemistry has on the selectivity between dielectric layer 103 and barrier layer 102.

For example, when dielectric layer 103 comprises silicon dioxide and barrier layer 102 comprises silicon nitride, an etch chemistry may be used to etch the trench that does not provide a high selectivity of silicon dioxide to silicon nitride. In addition, because this embodiment of the present invention reduces the amount of time during which barrier layer 102 is etched during the trench etch process, the thickness of barrier layer 102, e.g., a silicon nitride layer, when initially deposited, may be reduced to less than about 600 angstroms.

When a dyed base material is used for SLAM 104, the lithography subsequently used to pattern lines and spaces may be improved by reducing the amount of substrate reflectivity. This ensures that substrate reflectivity will be more uniform and controllable, which enables better CD control. Better CD control should enable use of sub 0.25 micron processes to make integrated circuits with dual damascene structures.

One method of the present invention thus allows for improved lithographic performance for defining line and space patterns, and allows for the use of an etch chemistry that enables vias and trenches with improved, substantially vertical, profiles to be formed—without regard to selectivity of the dielectric layer to the underlying barrier layer. In addition, by allowing for the use of a thinner barrier layer than might otherwise be required, this embodiment of the present invention may enable the making of a device having improved dielectric properties.

After trench 106 is etched, cleaning procedures follow to remove photoresist 136 and residues that may remain on the device's surface and inside the vias. Photoresist 136 may be removed using a conventional ashing procedure. Following such an ashing procedure, to ensure removal of remaining portions of SLAM 104, a wet etch procedure having a significantly higher selectivity for SLAM 104 over dielectric layer 103 should be used. When dielectric layer 103 comprises silicon dioxide and SLAM 104 comprises SOG, a 50:1 buffered oxide etch process should ensure that the remaining SOG material is removed at a substantially faster rate than the silicon dioxide. Alternatively, depending upon the type of SOG or SOP, and dielectric material used, other wet etch chemistry may be used, e.g., chemistry based on commercially available amine based materials. Irrespective of the chemistry chosen for the wet etch, high selectivity between the sacrificial layer and the dielectric layer must be maintained.

Barrier layer 102 protects conductive layer 101 from exposure to the solvents and/or oxidizing environment used when cleaning the trench. After that cleaning procedure, the portion of barrier layer 102 that separates via 107 from conductive layer 101 may be removed to expose conductive layer 101. A low polymer producing chemistry is preferably used to remove that portion of barrier layer 102, as is well understood by those skilled in the art.

Figure 2G:
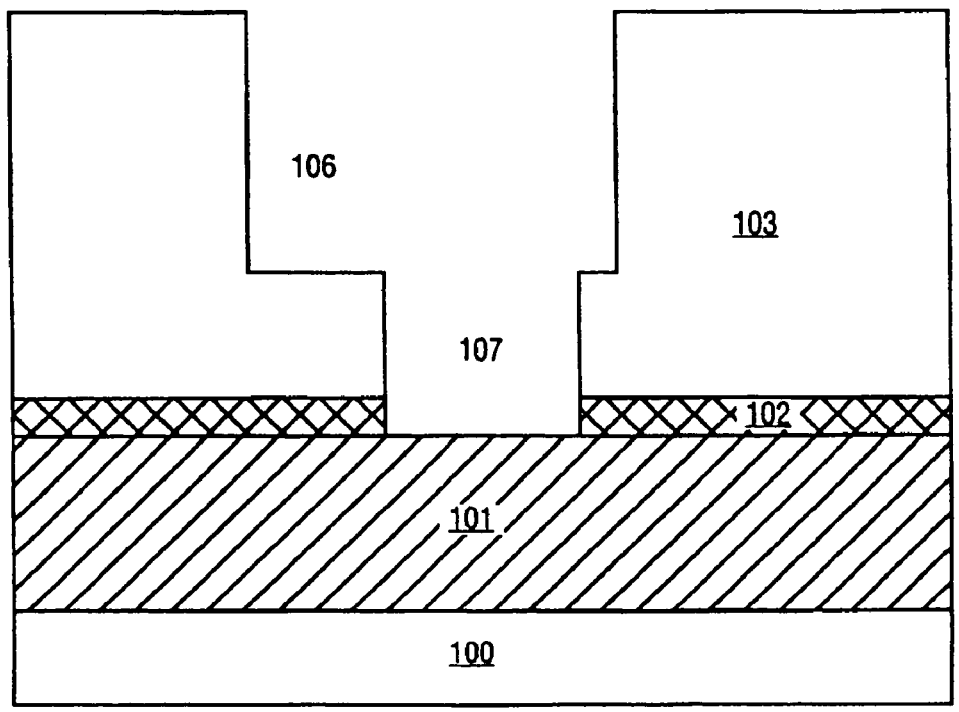

Barrier layer 102 removal may be followed by a short wet etch (which employs an etch chemistry that is compatible with the material used to form conductive layer 101) to clear etch residue from the surface of conductive layer 101. When copper is used to make the conductive layers, that portion of barrier layer 102 should be removed, using a copper compatible chemistry, before any copper electroplating procedure is applied to fill via 107 and trench 106. Removal of barrier layer 102 produces the structure shown in FIG. 2G.

Following that barrier layer removal procedure, trench 106 and via 107 are filled with second conductive layer 105.

Conductive layer 105 may comprise any of the materials identified above in connection with conductive layer 101. Conductive layer 105 may comprise the same conductive material as conductive layer 101, or may comprise a conductive material different from the material used to make conductive layer 101.

Conductive layer 105 preferably comprises copper, and is formed using a conventional copper electroplating process, in which a copper layer is formed on barrier and seed layers used to line trench 106 and via 107. The barrier layer may comprise a refractory material, such as titanium nitride, but may also include an insulating material, such as silicon nitride. Such an insulating barrier layer should be removed from the bottom of the via to allow conductive layer 105 to contact the underlying metal. The barrier layer formed beneath conductive layer 105 preferably is between about 100 and 500 angstroms thick. Suitable seed materials for the deposition of copper include copper and nickel.

As with conductive layer 101, although copper is preferred, conductive layer 105 may be formed from various materials that can serve to conduct electricity within an integrated circuit. When an excess amount of the material used to make layer 105 is formed on the surface of dielectric layer 103, a CMP procedure may be applied to remove the excess material and to planarize the surface of layer 105. When an electroplating process is used to form conductive layer 105 from copper, that CMP procedure removes both the excess copper and the underlying barrier layer. When dielectric layer 103 comprises silicon dioxide, that layer provides a CMP stop layer for such a CMP procedure.

Figure 2H:
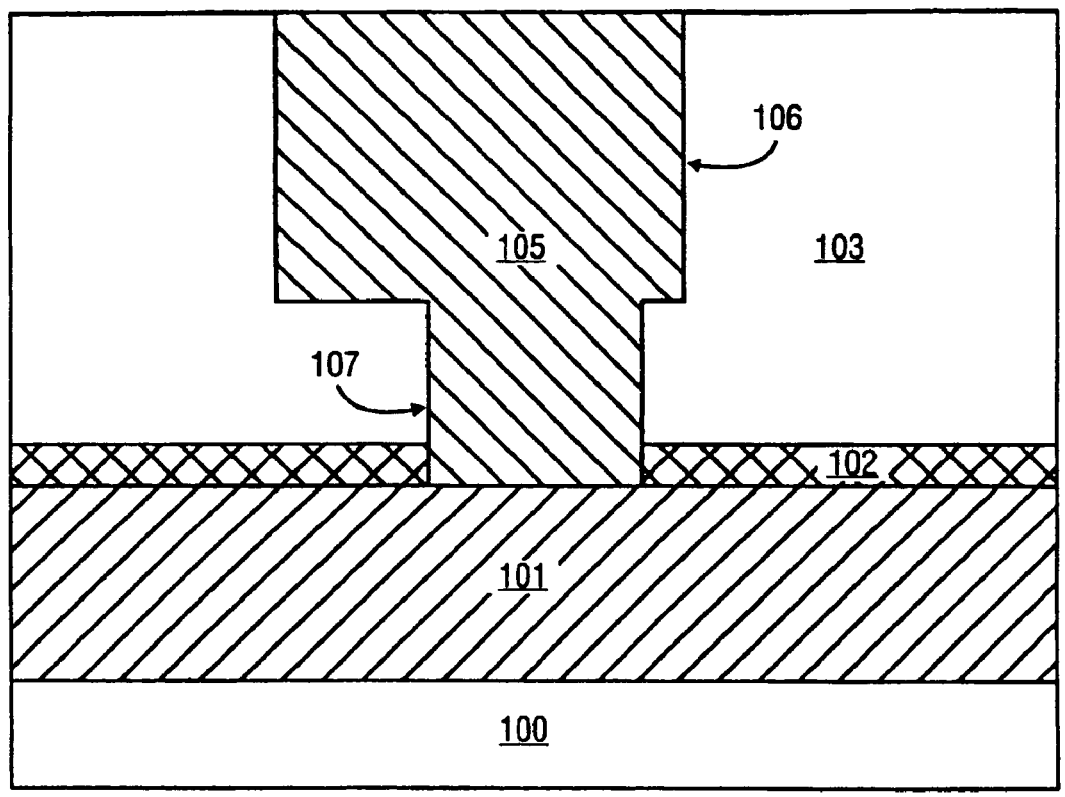

FIG. 2H shows the structure that results after filling trench 106 and via 107 with a conductive material, then applying a CMP procedure to remove excess material from the surface of layer 103 to produce conductive layer 105. Although the embodiment shown in FIG. 2H shows only one dielectric layer and two conductive layers, the process described above may be repeated to form additional conductive and insulating layers until the desired integrated circuit is produced.

Figure 3A:
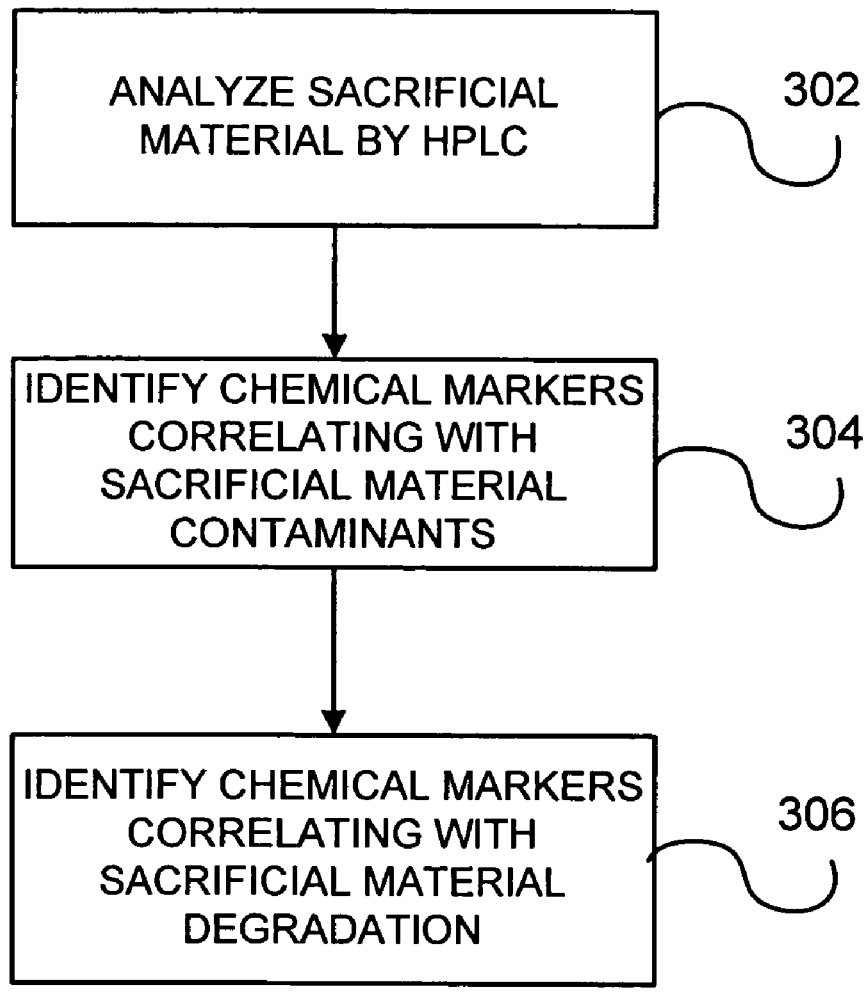
FIGS. 3A-3C are flow charts illustrating alternative methods to assay sacrificial materials.
Figure 3B:
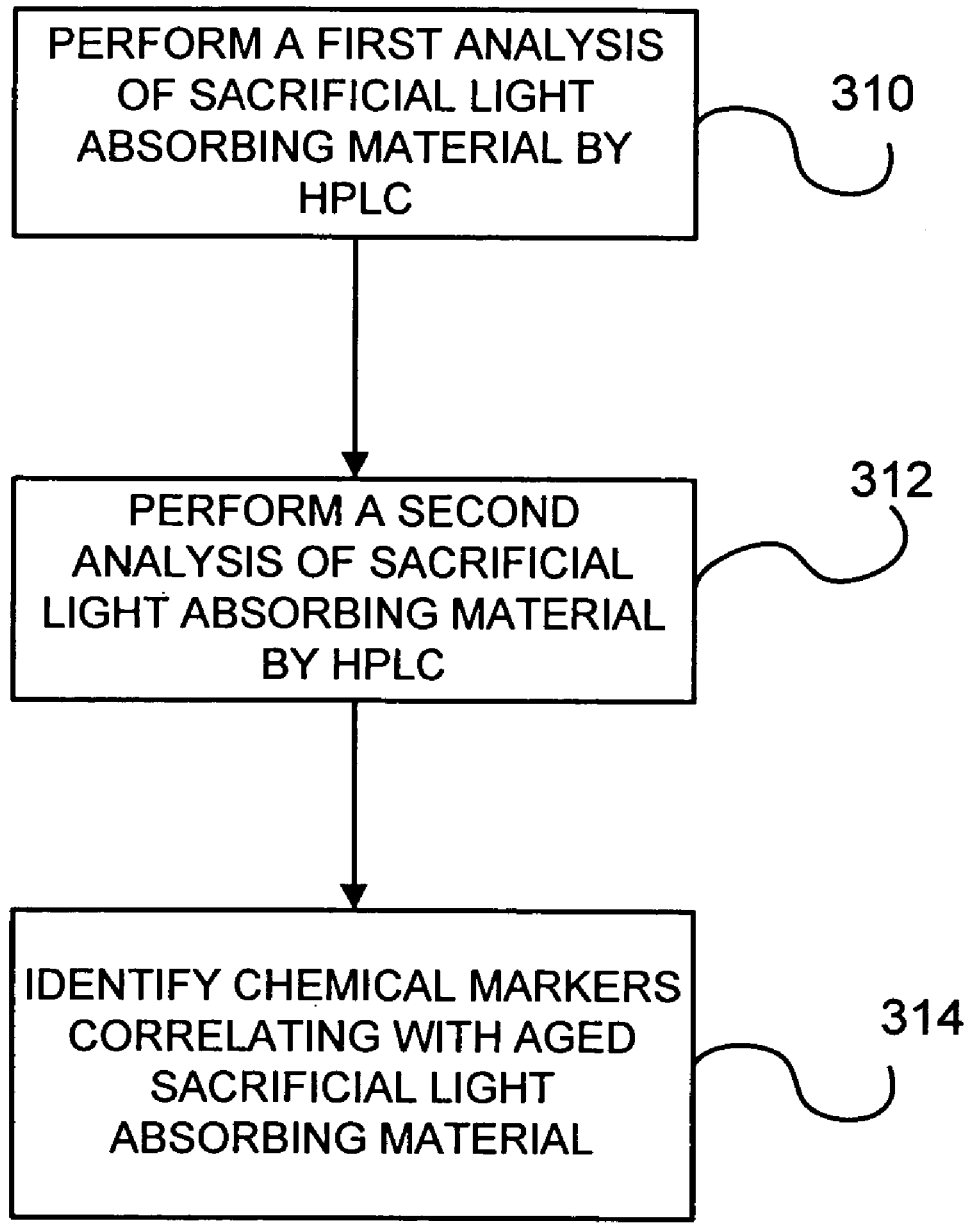
Figure 3C:
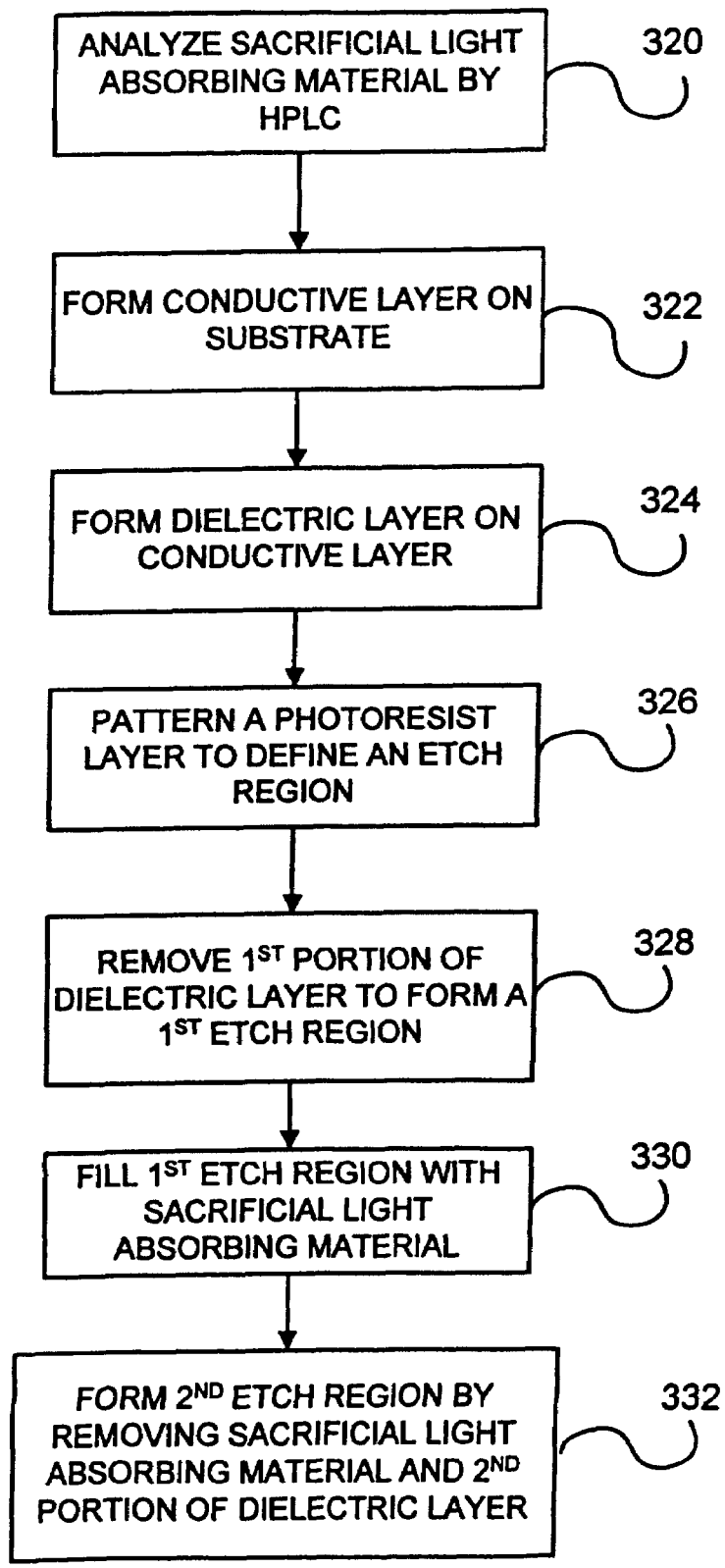

FIGS. 3A-3C illustrate alternative methods for the assay of sacrificial or dyed coating material to detect material defects. In one method, a sacrificial material may analyzed by HPLC to identify material defects, block 302. The sacrificial material may a sacrificial light absorbing material or other types of dyed coating materials such as SOG that may be used in semiconductor fabrication. Analysis by HPLC allows for the identification of chemical markers correlating with material contaminants (e.g., FIG. 1B), block 304. Contaminants may adversely affect sacrificial material performance during a semiconductor fabrication process (e.g., dual damascene). Analysis by HPLC also allows for identifying chemical markers correlating with material degradation (e.g., FIG. 1C), block 306. In one embodiment, an ultraviolet/visual and mass spectroscopy system may be used following the HPLC assay to identify the chemical markers correlating with SLAM and contaminant material. The monitoring wavelength of the UV/VIS detector for SLAM may be between about 240 nanometers to about 260 nanometers.

FIG. 3B illustrates an alternative method for the assay of sacrificial or dyed coating material to detect material defects. A first analysis or assay by HPLC is performed on a SLAM sample, block 310. This first analysis may indicate a clean, uncontaminated SLAM sample (e.g., FIG. 1A). A second analysis by HPLC is performed on the same SLAM sample, block 312. In one method, the second analysis is done after a certain period of time (e.g., 10 days after the first analysis). A comparison between the first HPLC assay and the second HPLC assay of the SLAM sample may identify chemical markers correlating with aged and/or degradation characteristics (e.g., FIG. 1C), block 314. In one embodiment, an ultraviolet/visual and mass spectroscopy system may be used following the HPLC assay to identify the chemical markers correlating with SLAM degradation. The monitoring wavelength of the UV/VIS detector for SLAM may be between about 240 nanometers to about 260 nanometers.

FIG. 3C illustrates an alternative method for the assay of sacrificial or dyed coating material to detect material defects during in process (i.e., during semiconductor fabrication process or dual damascene). A SLAM sample is analyzed/assayed by HPLC, block 320. An ultraviolet/visual and mass spectroscopy system may be used following the HPLC assay to identify the chemical markers. For example, the HPLC assay may indicate a clean uncontaminated SLAM sample, identification material defects, or SLAM degradation over time. A conductive layer is formed on a substrate, block 322, then a dielectric layer on the conductive layer, 324. After forming the dielectric layer, a layer of photoresist is patterned to define a region to be etched, block 326. A first etched region is then formed by removing a first portion of the dielectric layer, block 328. That first etched region is filled with a SLAM, block 330. In one embodiment, the SLAM has dry etch properties similar to those of the dielectric layer. A second etched region is then formed by removing the sacrificial material and a second portion of the dielectric layer, block 332.

In the foregoing specification, the invention has been described with reference to specific exemplary embodiments thereof. It will, however, be evident that various modifications and changes may be made thereto without departing from the broader spirit and scope of embodiments of the invention as set forth in the appended claims. The specification and figures are, accordingly, to be regarded in an illustrative rather than a restrictive sense.

What is claimed is:

1. A method, comprising:
analyzing a sacrificial light absorbing material with high performance liquid chromatography to identify whether the sacrificial light absorbing material contains a material contaminant or has degraded;
forming a conductive layer on a substrate;
forming a dielectric layer on the conductive layer;
patterning a layer of photoresist, after forming the dielectric layer, to define a region to be etched;
forming a first etched region by removing a first portion of the dielectric layer;
filling the first etched region with the sacrificial light absorbing material; and
forming a second etched region by removing the sacrificial light absorbing material and a second portion of the dielectric layer.

2. The method of claim 1, wherein analyzing further comprises detecting chemical markers that correlate to the sacrificial light absorbing material with an ultraviolet/visual and mass spectroscopy system.

3. The method of claim 2, wherein the ultraviolet/visual and mass spectroscopy system has a monitoring wavelength of about 240 nanometers to about 260 nanometers.

4. The method of claim 1, wherein the sacrificial light absorbing material is selected from the group consisting of a dyed SOP and a dyed SOG and that has dry etch properties similar to those of the dielectric layer.

5. The method of claim 1, wherein sacrificial light absorbing material is analyzed prior to filling the first etched region.

6. The method of claim 1 wherein the sacrificial material has the following properties:
- it may be dry etched at substantially the same rate that the dielectric layer may be dry etched;
- it may be wet etched at a significantly faster rate than the dielectric layer may be wet etched;
- it may absorb light having a wavelength that is identical to the wavelength used to expose the photoresist to pattern it; and
- it may completely and uniformly fill the first etched region.

7. The method of claim 4 further comprising:
- forming a barrier layer on the surface of the conductive layer prior to forming the dielectric layer;
- forming the first and second etched regions without first forming a second barrier layer on the surface of the dielectric layer;
- removing part of the barrier layer after forming the second etched region; and
- filling the first and second etched regions with a second conductive layer.

8. The method of claim 4, wherein the integrated circuit includes a dual damascene interconnect, and wherein the first etched region forms the via for the interconnect and the second etched region forms the trench for the interconnect.

9. The method of claim 4, wherein the integrated circuit includes a dual damascene interconnect, and wherein the first etched region forms the trench for the interconnect and the second etched region forms the via for the interconnect.

10. The method of claim 1 wherein analyzing the sacrificial light absorbing material with high performance liquid chromatography further comprises:
- analyzing the sacrificial light absorbing material with high performance liquid chromatography a first time to generate a first signal;
- analyzing the sacrificial light absorbing material with high performance liquid chromatography a second time to generate a second signal;
- comparing the first signal to the second signal to identify whether the sacrificial light absorbing material has degraded; and
- determining that the sacrificial light absorbing material has not degraded.

11. The method of claim 10, wherein the sacrificial light absorbing material has degraded if the second signal is broader than the first signal, and the sacrificial material has not degraded if the second signal is not broader than the first signal.

12. The method of claim 1 wherein analyzing the sacrificial light absorbing material with high performance liquid chromatography further comprises:
- assaying the sacrificial light absorbing material with high performance liquid chromatography to generate a chromatogram;
- analyzing the chromatogram to identify whether a chemical marker exists in the chromatogram that correlates with a material contaminant in the sacrificial light absorbing material.

13. The method of claim 12, further comprising determining that the chemical marker does not exist in the chromatogram prior to forming the conductive layer on a substrate.

14. The method of claim 12, further comprising determining that the chemical marker does exist in the chromatogram.

15. The method of claim 14, further comprising:
- performing one or more cleaning techniques followed by assaying the sacrificial light absorbing material with high performance liquid chromatography to generate a second chromatogram;
- analyzing the second chromatogram to identify whether a chemical marker exists in the second chromatogram that correlates with a material contaminant in the sacrificial light absorbing material; and
- determining that the chemical marker does not exist in the second chromatogram prior to forming the conductive layer on a substrate.

* * * * *